United States Patent [19]

Bauer et al.

[11] Patent Number: 5,362,730
[45] Date of Patent: * Nov. 8, 1994

[54] TERAZOSIN POLYMORPH AND PHARMACEUTICAL COMPOSITION

[75] Inventors: John F. Bauer, Lake Bluff; James A. Morley, Gurnee, both of Ill.

[73] Assignee: Abbott Laboratories, Abbott Park, Ill.

[ * ] Notice: The portion of the term of this patent subsequent to Mar. 15, 2011 has been disclaimed.

[21] Appl. No.: 178,184

[22] Filed: Jan. 6, 1994

Related U.S. Application Data

[63] Continuation-in-part of Ser. No. 90,721, Jul. 13, 1993, Pat. No. 5,294,615, which is a continuation-in-part of Ser. No. 54,917, Apr. 29, 1993, abandoned.

[51] Int. Cl.$^5$ ............... A61K 31/505; C07D 239/84
[52] U.S. Cl. ..................................... 514/254; 544/291
[58] Field of Search ..................... 544/291; 514/254

[56] References Cited

U.S. PATENT DOCUMENTS

| | | | |
|---|---|---|---|
| 4,026,894 | 5/1977 | Winn et al. | 424/251 |
| 4,112,097 | 9/1978 | Winn et al. | 424/251 |
| 4,251,532 | 2/1981 | Roteman | 424/251 |
| 5,212,176 | 5/1993 | Kyncl et al. | 514/254 |

*Primary Examiner*—Cecilia Tsang
*Attorney, Agent, or Firm*—Jerry F. Janssen

[57] ABSTRACT

A process for preparing a novel anhydrous crystalline polymorph of anhydrous 1-(4-amino-6,7-dimethoxy-2-quinazolinyl)-4-(tetrahydro-2-furoyl)piperazine monohydrochloride comprises contacting the known amorphous, crystalline dihydrate, or crystalline anhydrous form I of the compound with a polar organic solvent.

13 Claims, 12 Drawing Sheets

TERAZOSIN POLYMORPH AND PHARMACEUTICAL COMPOSITION

Cross-Reference to Related Applications

This application is a continuation-in-part of copending application Ser. No. 08/090,721 filed Jul. 13, 1993, now U.S. Pat. No. 5,294,615 which, in turn, is a continuation-in-part of application Ser. No. 08/054,917 filed Apr. 29, 1993, now abandoned.

TECHNICAL FIELD

This invention relates to a method for preparing a particular anhydrous crystalline polymorph of 1-(4-amino-6,7-dimethoxy-2-quinazolinyl)-4-(tetrahydro2-furoyl)piperazine monohydrochloride ("terazosin" hydrochloride) and to the product of that process.

BACKGROUND OF THE INVENTION

The compound 1-(4-amino-6,7-dimethoxy-2-quinazolinyl)-4-(tetrahydro-2furoyl)piperazine is known by the common name "terazosin" and is the subject of U.S. Pat. No. 4,026,894. This patent discloses in Example VI a process for making the anhydrous crystalline polymorph of terrazosin designated "form I" throughout this application. The compound is known to have utility for the treatment of hypertension and benign prostatic hyperplasia, and pharmaceutical compositions comprising terazosin and its salts are claimed in U.S. Pat. No. 4,112,097. The dihydrate crystalline form of the hydrochloride salt of terazosin is disclosed and claimed in U.S. Pat. No. 4,251,532, and is marketed under the trade name Hytrin ®. The R(+)-enantiomer of terazosin is disclosed and claimed in U.S. Pat. No. 5,212,176.

BRIEF DESCRIPTION OF THE DRAWING

In the draining.

SUMMARY OF THE INVENTION

The present invention provides, in its principle embodiment, a process for preparing a particularly stable anhydrous crystalline polymorph of 1-(4-amino-6,7-dimethoxy-2-quinazolinyl)-4-(tetrahydro-2-furoyl)piperazine monohydrochloride which is free of both the prior an crystalline anydrate form I and the prior art crystalline dihydrate. The process of this invention comprises contacting a material selected from the group consisting of crystalline 1-(4-amino-6,7-dimethoxy-2-quinazolinyl)-4-(tetrahydro-2-furoyl)piperazine e monohydrochloride dihydrate, crystalline 1-(4-amino-6,7-dimethoxy-2-quinazolinyl)-4-(tetrahydro-2furoyl)-piperazine e monohydrochloride anhydrate form I, and amorphous 1-(4-amino-6,7-dimethoxy-2-quinazolinyl)-4-(tetrahydro-2-furoyl)piperazine monohydrochloride with an anhydrous polar organic solvent, followed by removal of the solvent to recover the solid product.

In another embodiment, the present invention provides the product of that process.

In a further embodiment of the present invention, there are provided pharmaceutical compositions comprising a therapeutically effective amount of the novel crystalline polymorph described above in combination with a pharmaceutically acceptable carrier.

Figure 1:
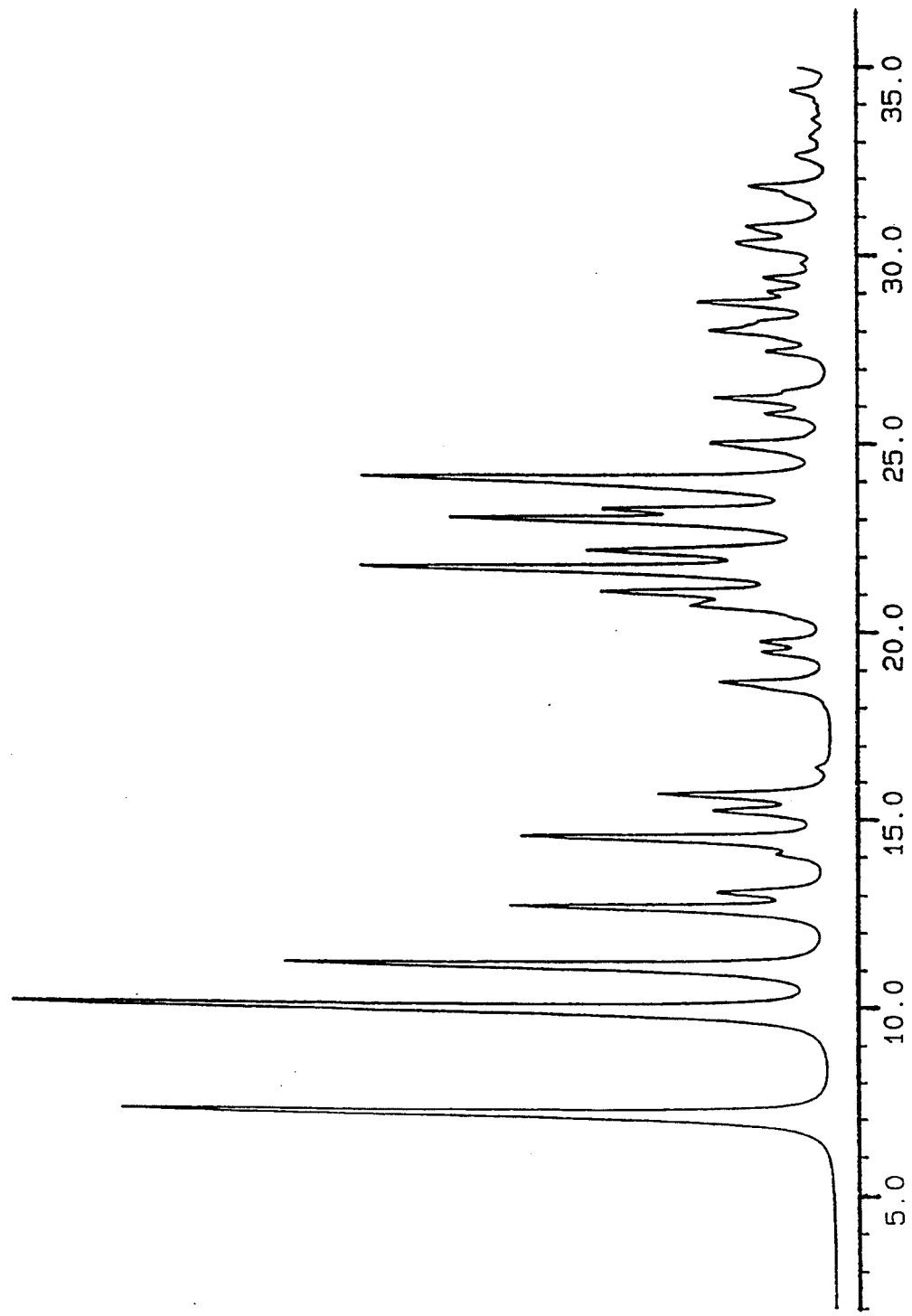
FIGS. 1, 4, 7, and 10 show, respectively, the powder X-ray diffraction pattern, the $^{13}C$ nuclear magnetic resonance spectrum, the infrared spectrum, and the differential scanning calorimetric thermogram of the prior art anhydrate ("form I") of 1-(4-amino-6,7-dimethoxy-2-quinazolinyl)-4-(tetrahydro-2-furoyl)piperazine monohydrochloride.
Figure 2:
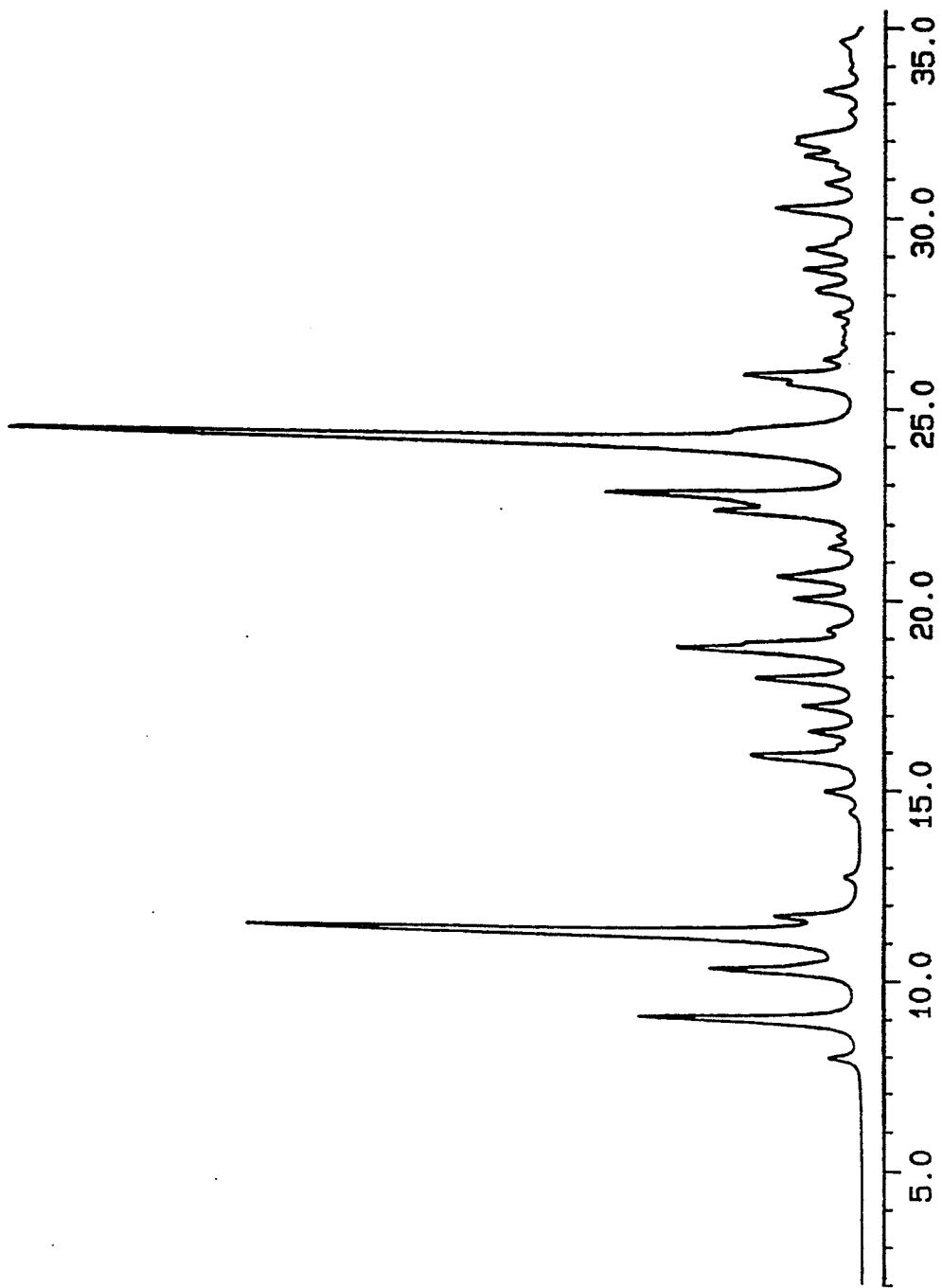
FIGS. 2, 5, 8, and 11 show, respectively, the powder X-ray diffraction pattern, the $^{13}C$ nuclear magnetic resonance spectrum, the infrared spectrum, and the differential scanning calorimetric thermogram of the prior art dihydrate form of 1-(4-amino-6,7-dimethoxy-2-quinazolinyl)-4-(tetrahydro-2-furoyl)piperazine monohydrochloride.
Figure 4:
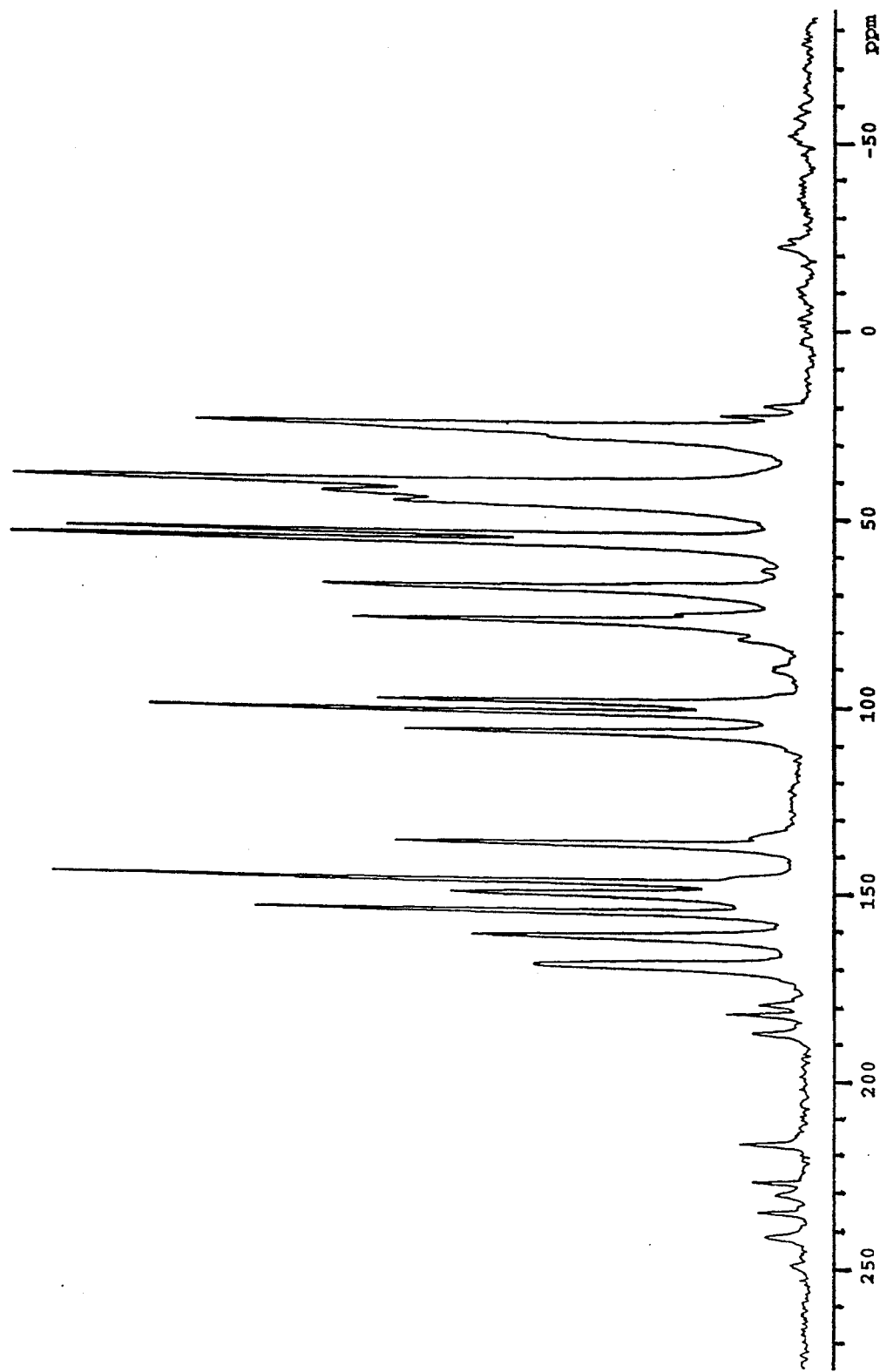
Figure 5:
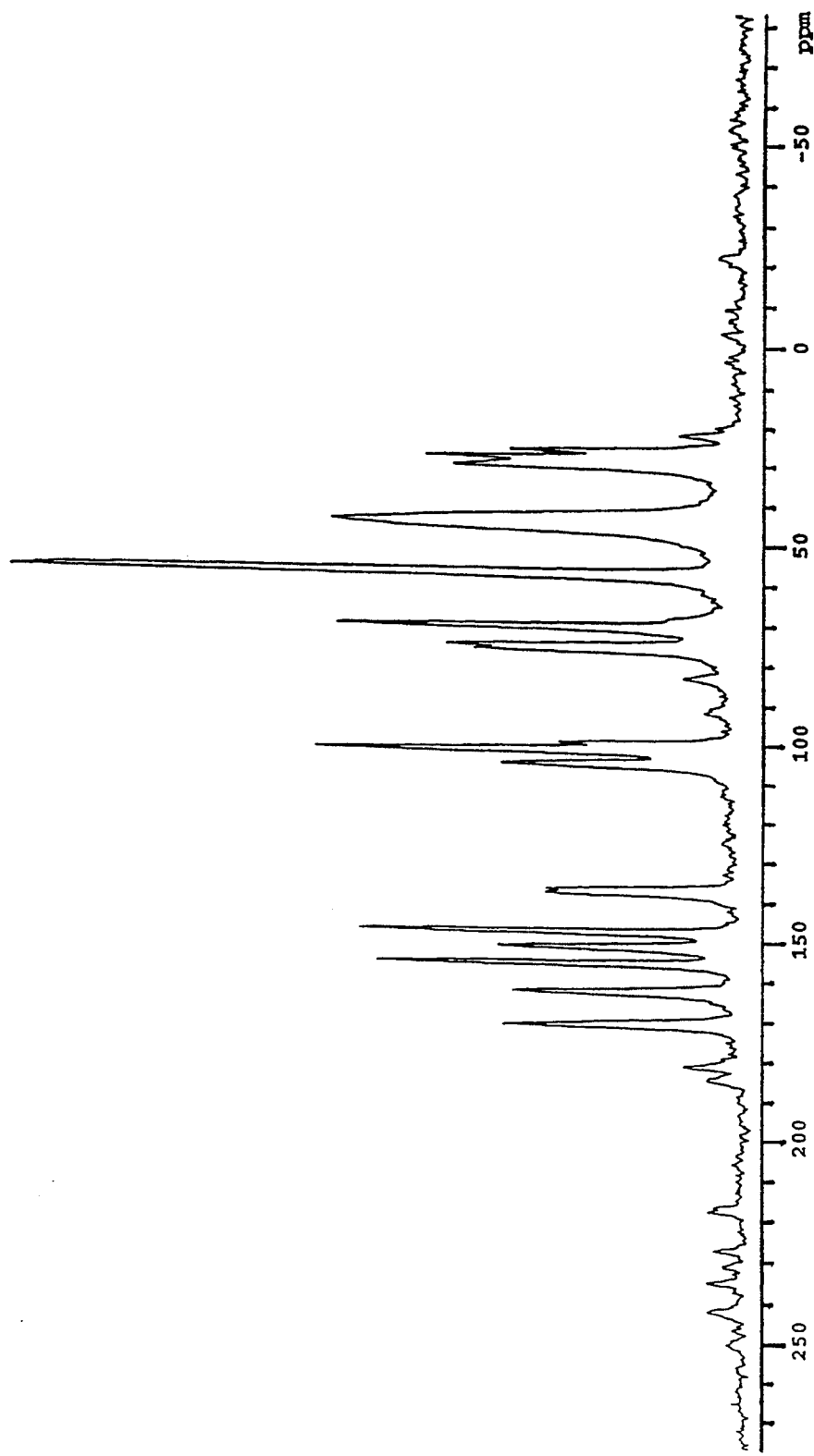
Figure 7:
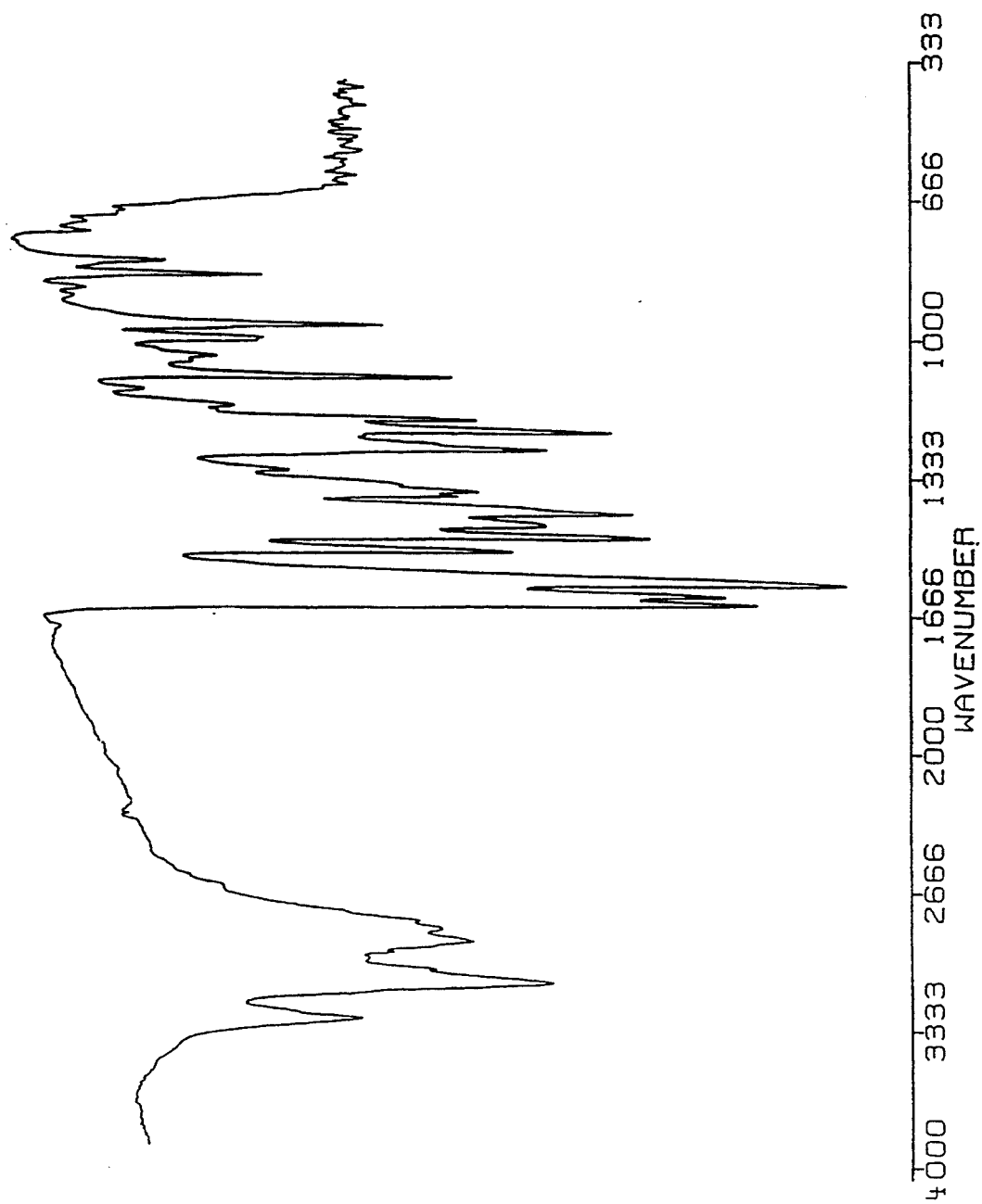
Figure 8:
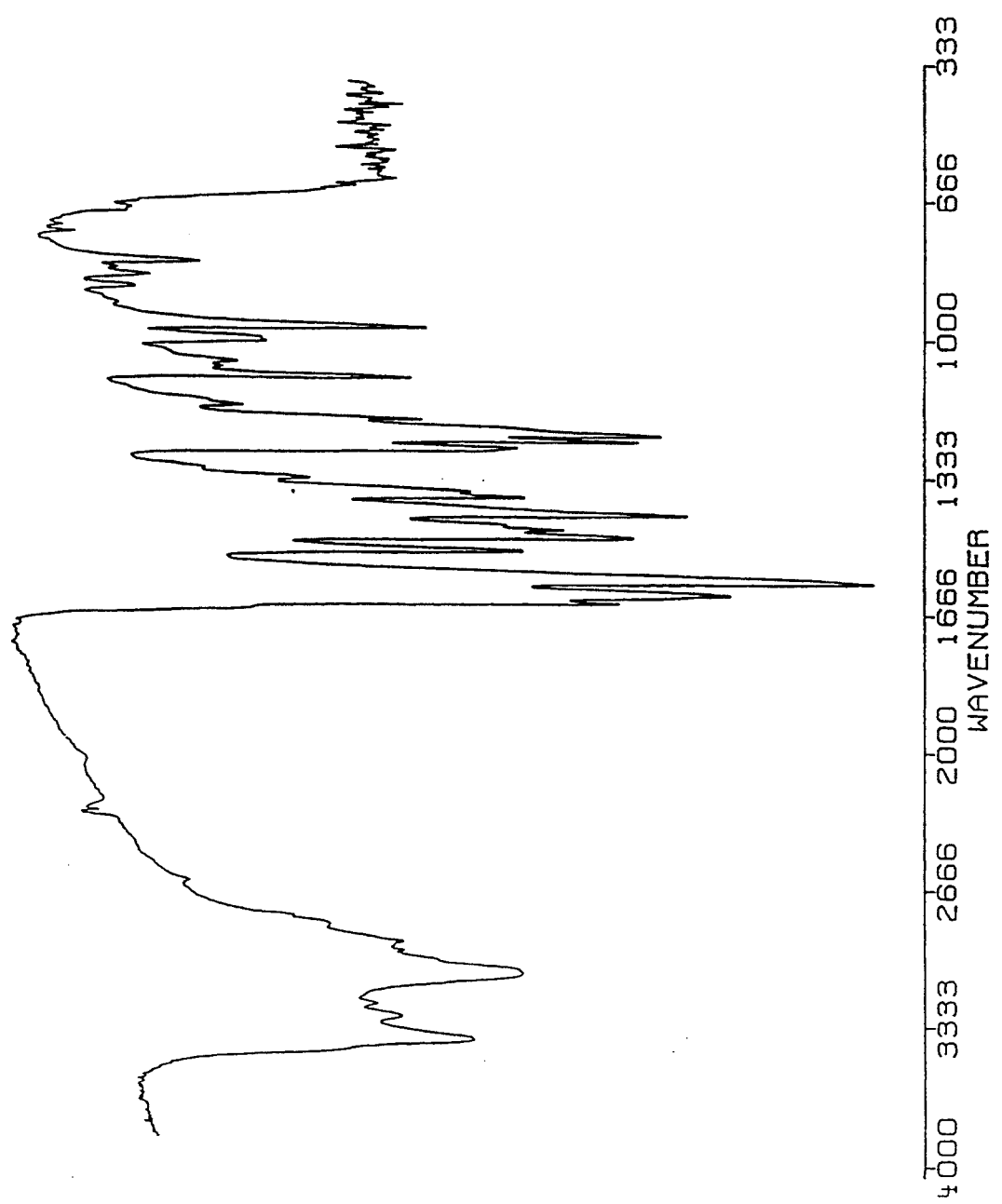
Figure 10:
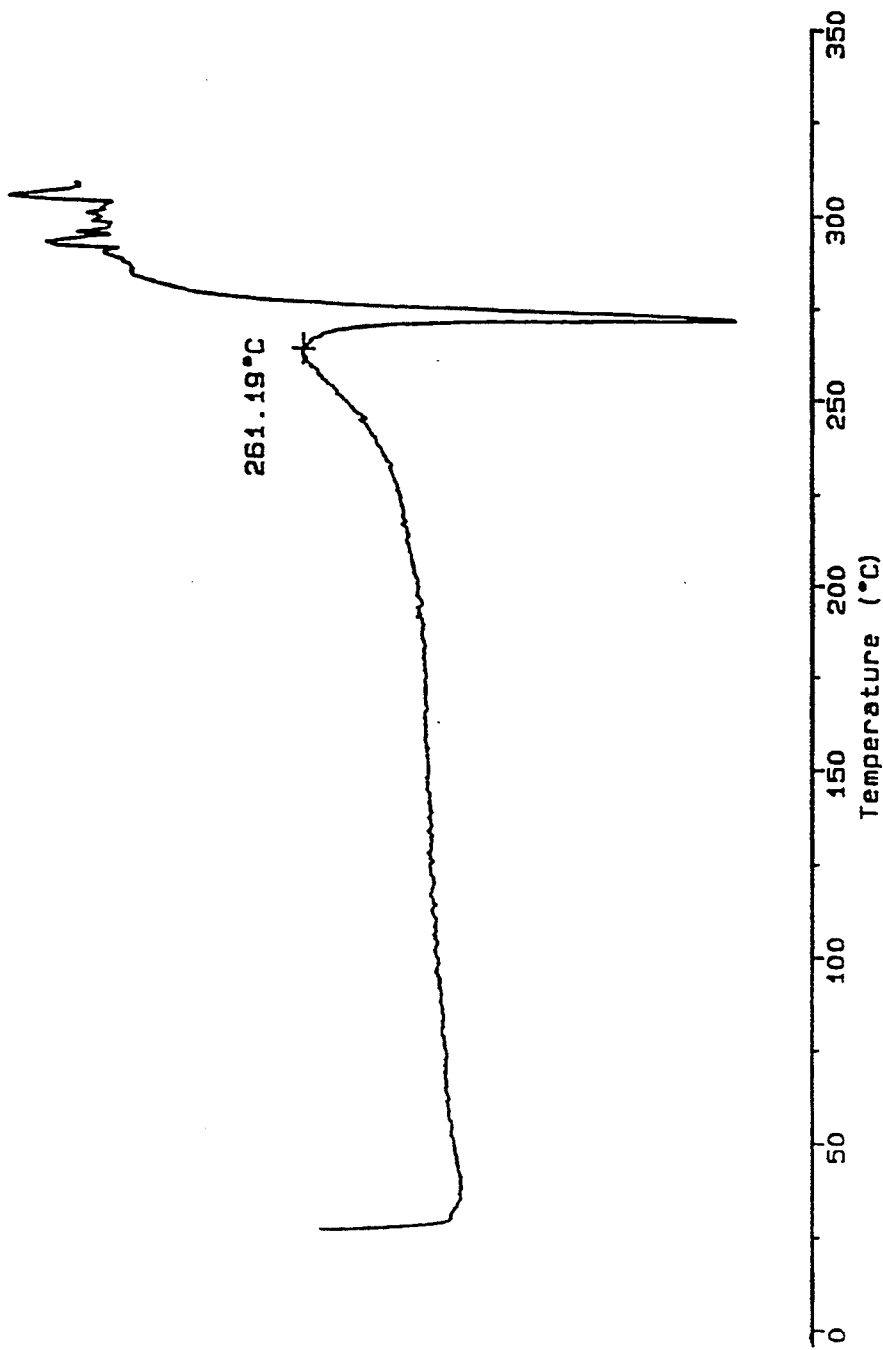
Figure 11:
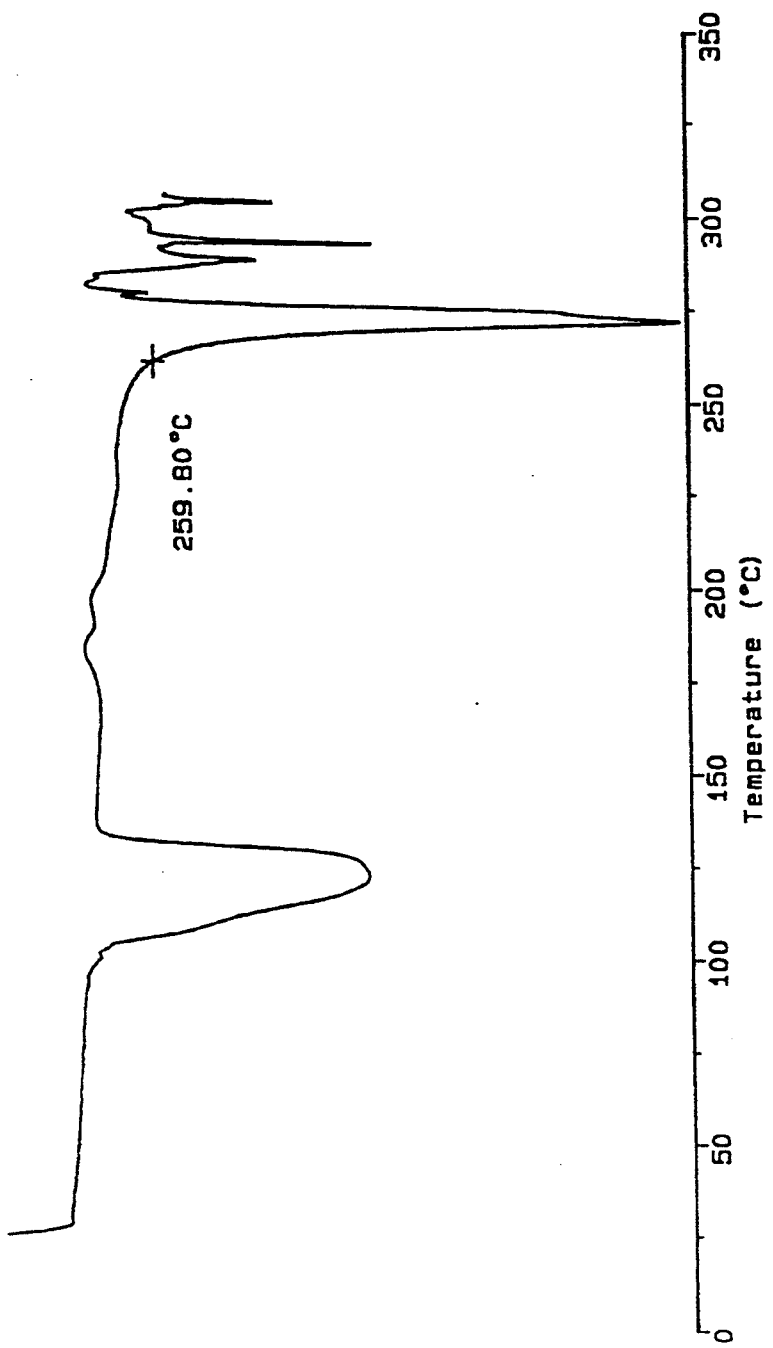

DETAILED DESCRIPTION 1-(4-Amino-6,7-dimethoxy-2-quinazolinyl)-4-(tetrahydro-2furoyl)piperazine monohydrochloride (also known by its generic name, "terazosin" monohydrochloride) is known to exist in several forms including an amorphous form, an anhydrous or anhydrate crystalline form ("form I") and a dihydrate crystalline form. The dihydrate form, disclosed in U.S. Pat. No. 4,251,532, is characterized by the data shown in FIGS. 2, 5, 8, and 11. When the dihydrate form is dried by conventional methods such as oven drying, the known amorphous form is produced. U.S. Pat. No. 4,026,894 discloses in Example VI a method for preparing the anhydrous crystalline modification termed "form I" throughout this specification and the appended claims. The crystalline anhydrate form I is characterized by the data which are presented in FIGS. 1, 4, 7, and 10.

Figure 3:
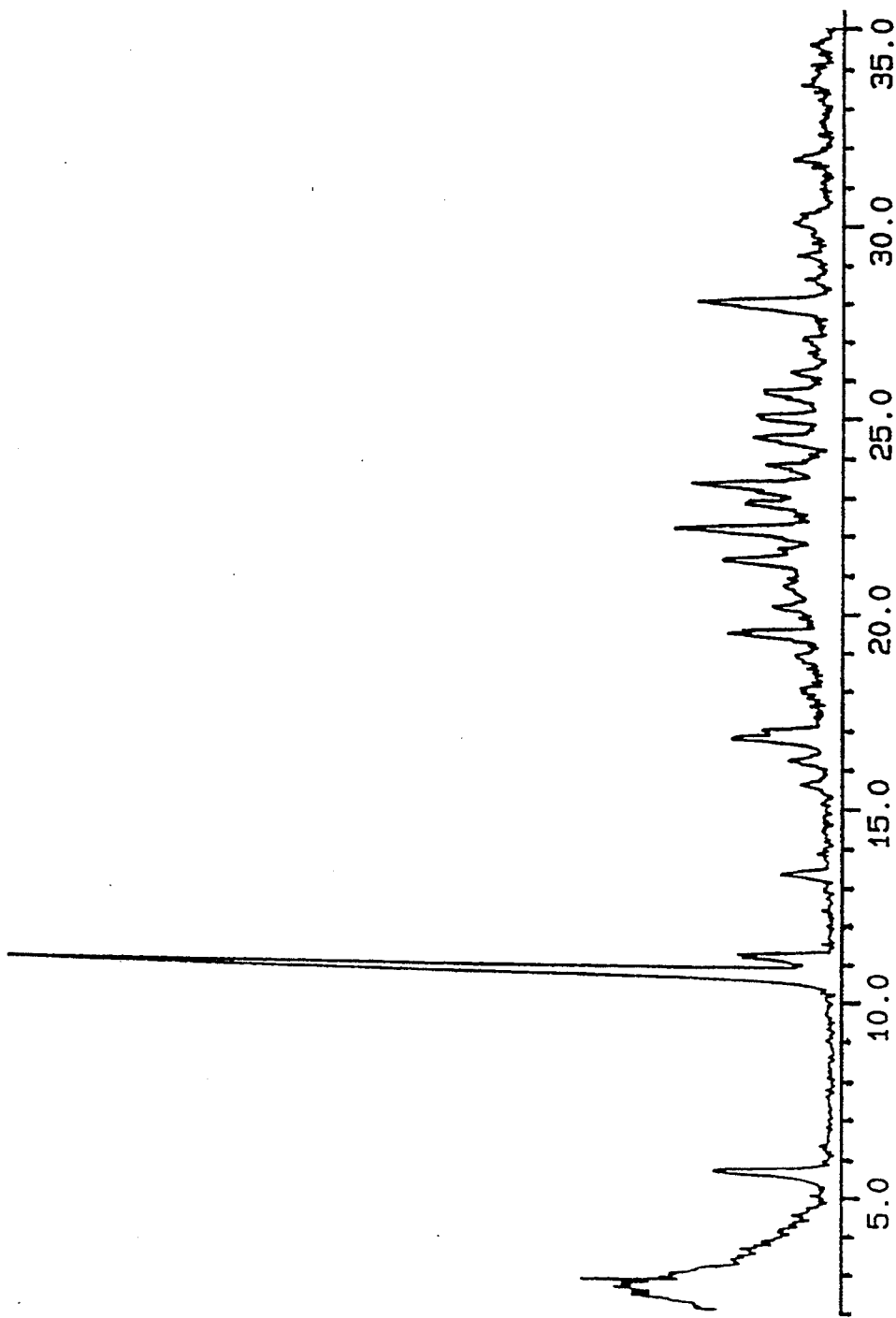
FIGS. 3, 6, 9, and 12 show, respectively, the powder X-ray diffraction pattern, the $^{13}C$ nuclear magnetic resonance spectrum, the infrared spectrum, and the differential scanning calorimetric thermogram of the form of 1-(4-amino-6,7-dimethoxy-2-quinazolinyl)-4-(tetrahydro-2-furoyl)piperazine monohydrochloride of the present invention ("form II").
Figure 6:
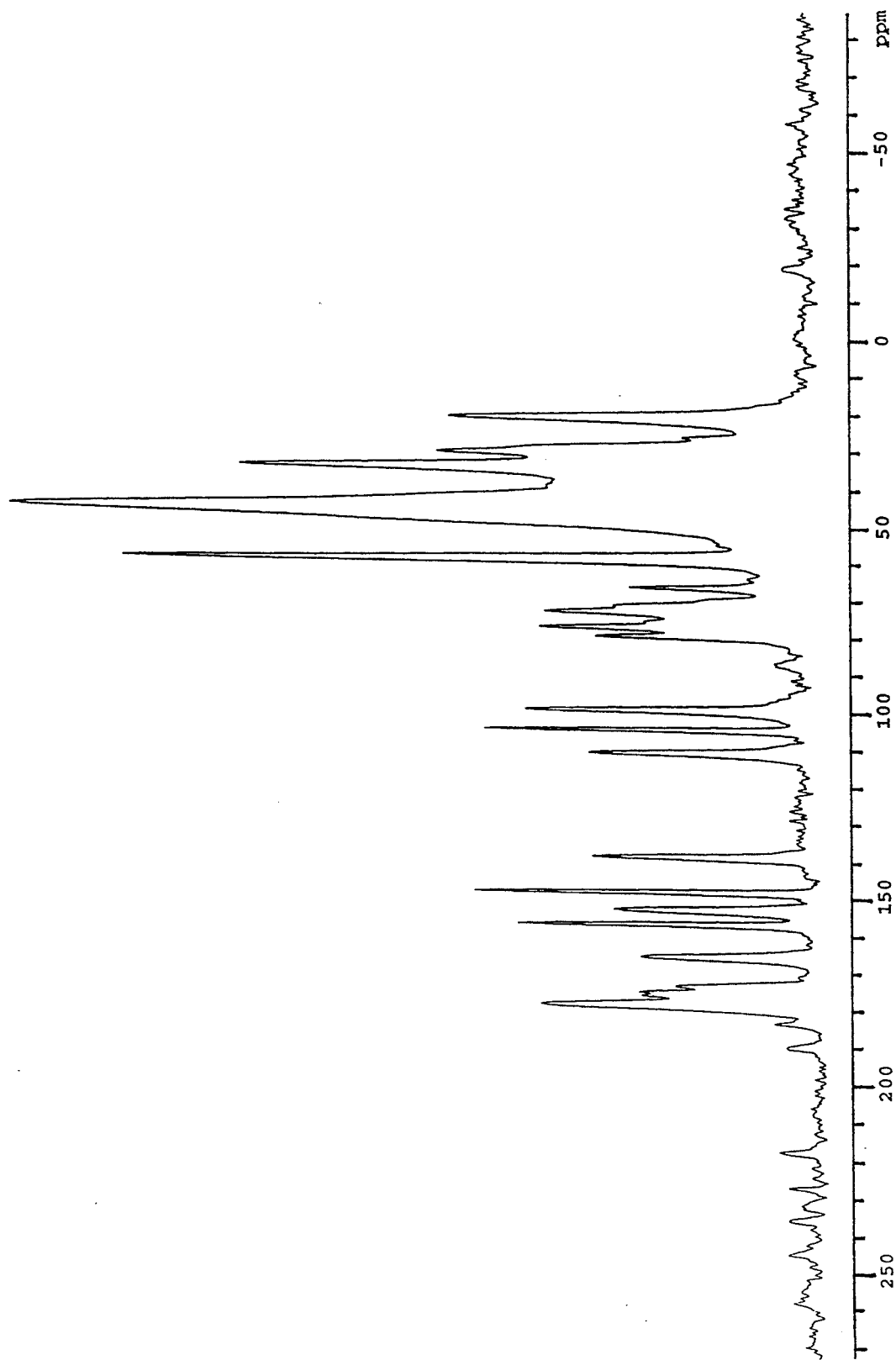
Figure 9:
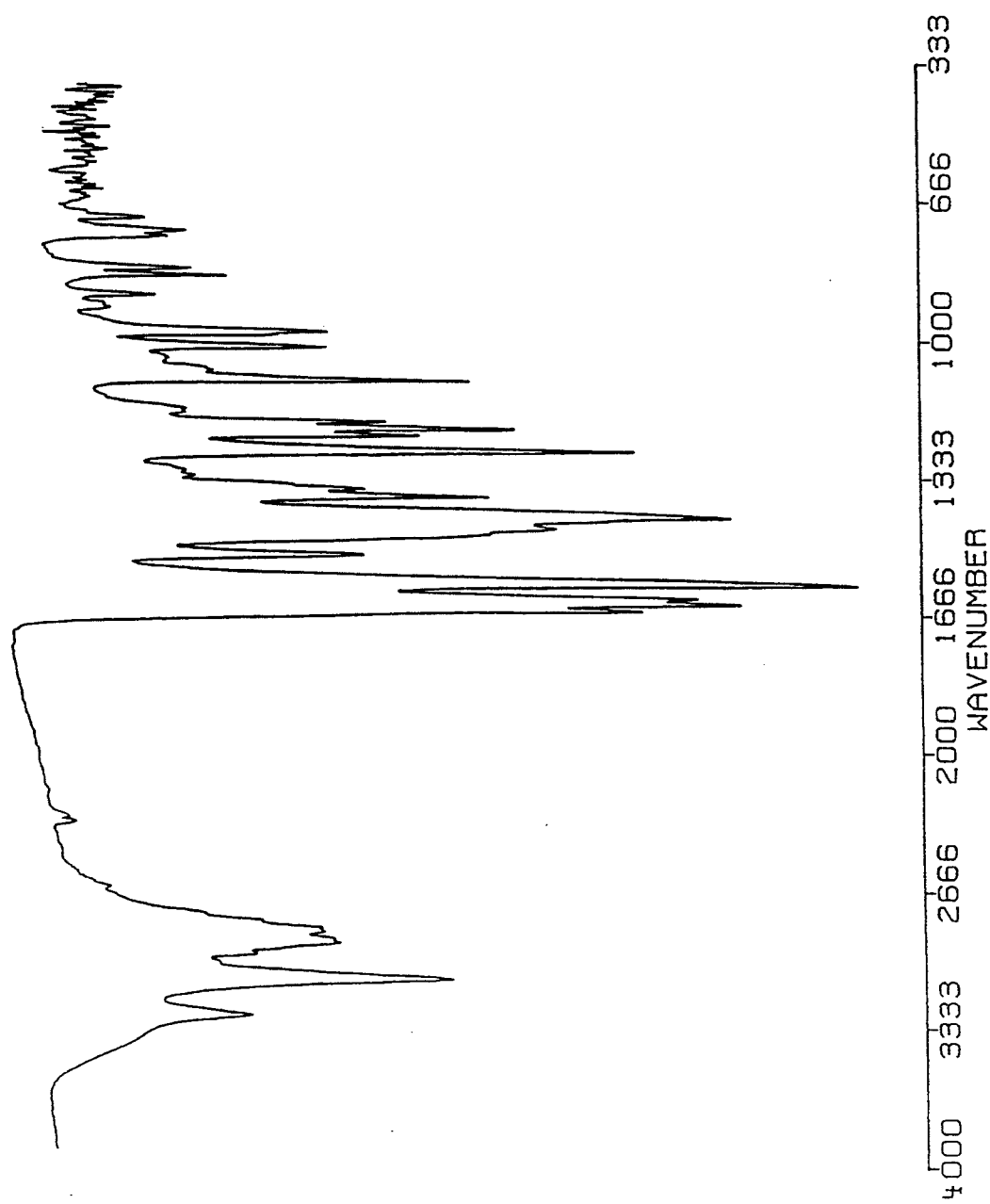
Figure 12:
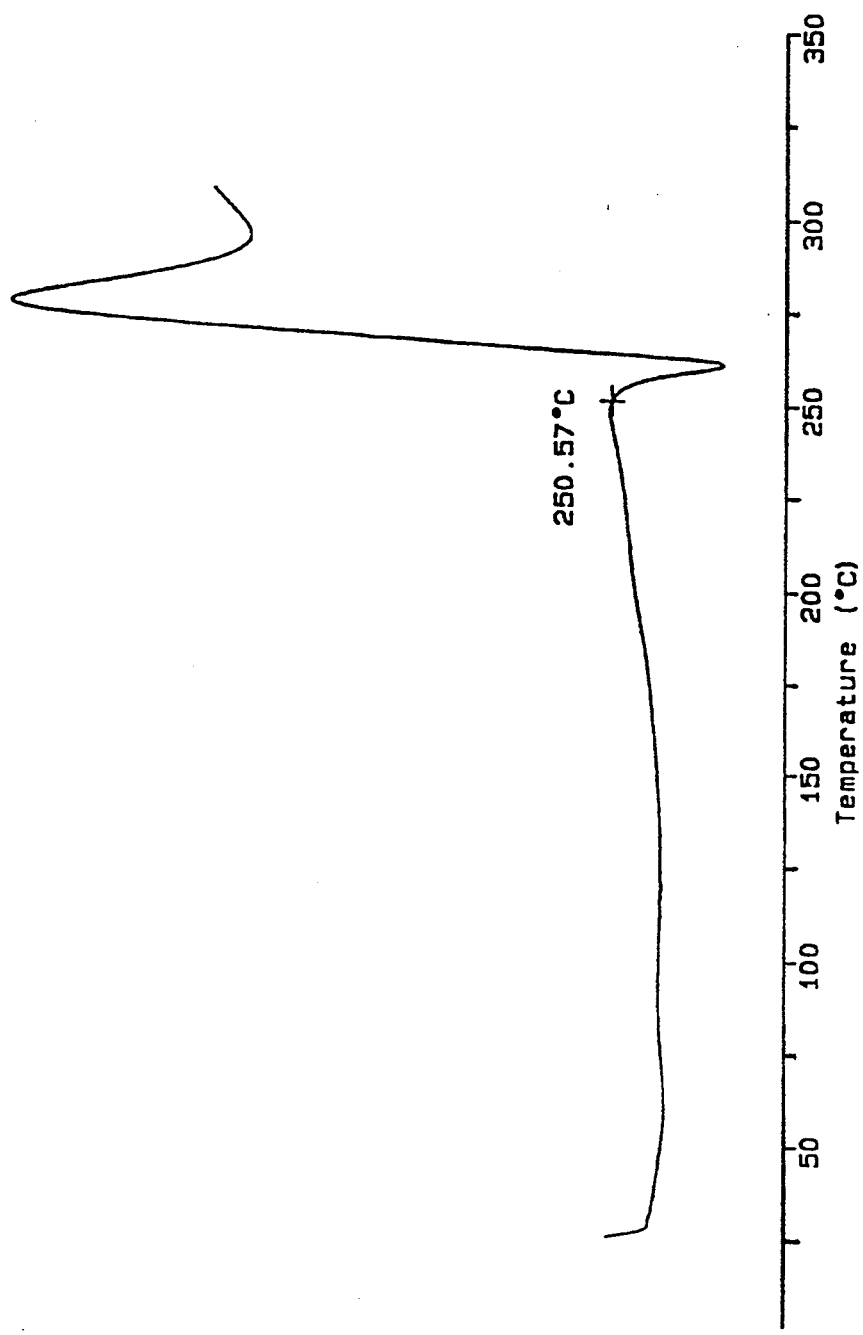

However, in accordance with the present invention, it has been unexpectedly found that when the previously known dihydrate crystalline form of terazosin, the crystalline anhydrate form I, or the amorphous form is contacted with a dry, polar organic solvent such as $C_1$–$C_6$ alcohols or $C_3$–$C_6$ ketones or mixtures thereof, each is converted to a particularly stable hitherto unknown anhydrous crystalline polymorph of terazosin of the present invention which is characterized by the powder X-ray diffraction pattern, $^{13}C$ nuclear magnetic resonance spectrum, infrared spectrum, and differential scanning calorimetric thermogram of FIGS. 3, 6, 9, and 12, respectively. For the sake of convenience, the anhydrous crysalline polymorph of terazosin monohydrochloride of this invention is designated throughout this specification and the appended claims as "form II" of the crystalline anhydrate.

The novel anhydrous crystalline polymorph of the present invention is prepared by either a "suspension" (or "reflux") process or a "solution process." In the suspension or reflux process, the known monohydrochoride dihydrate crystalline form of 1-(4-amino-6,7-dimethoxy-2-quinazolinyl)-4-(tetrahydro-2-furoyl)piperazine is suspended in a dry, polar organic solvent such as a $C_1$–$C_6$ alcohol or $C_3$–$C_6$ ketone or mixtures thereof. Particularly useful in this variant of the process of the invention are absolute ethanol or dry acetone. The suspension is heated under reflux for a period sufficient to remove the water of crystallization and to convert the undissolved solid to the anhydrous crystalline polymorph. Generally, this requires a period of from about ten hours to five days.

In the so-called "solution" process, the novel anhydrous crystalline polymorph of the present invention is prepared by recrystallizing either the monohydrochloride dihydrate crystalline form of terazosin or the crystalline anhydrous (form I) of terazosin from a polar organic solvent such as a $C_1$-$C_6$ alcohol or $C_3$-$C_6$ ketone or mixtures thereof. For this variant of the process of this invention, the lower, more polar, alcohols such as methanol and ethanol are preferred. The solid starting material is dissolved in the hot solvent and the desired product collected by filtration upon cooling. Alternatively, the starting solid may be dissolved in the minimum amount of alcohol followed by addition of acetone or other miscible polar dry organic solvent to effect precipitation of the anhydrous crystalline form.

The solvents employed for this process are selected from $C_1$-$C_6$ alcohols or $C_3$-$C_6$ ketones or mixtures thereof such as acetone, methyl ethyl ketone ("MEK"), diethyl ketone, and alcohols such as methanol, ethanol, propanol, isopropanol, n-butanol, sec-butanol, iso-butanol and the like. Preferred solvents are methanol, ethanol and acetone. The solvents are carefully dried prior to use by methods well known in the art such as contacting them with dehydrating alumnosilicate or aluminophosphate zeolites, commonly called "molecular sieves." The molecular sieves are chosen from those grades having a pore size which is optimized for trapping water molecules, preferably about 4 Å units. The solvent is allowed to stand at room temperature over the molecular sieves until dry, generally for a period of from about 24 to about 48 hours. An additional drying step may be taken which consists of contacting the molecular sieve-dried solvent with anhydrous magnesium or sodium sulfate or of filtering the molecular sieve-dried solvent through a pad of anhydrous magnesium or sodium sulfate prior to use. The water content of the solvents can be checked by well known methods such as the Karl Fischer method (*Angew. Chem.*, 48:394 (1935); D. Smith, et al., *J. Am. Chem. Soc.*, 61:2407 (1939)).

The present invention also provides pharmaceutical compositions which comprise the novel anhydrous crystalline polymorph of terazosin of this invention formulated together with one or more non-toxic pharmaceutically acceptable carders. The pharmaceutical compositions may be specially formulated for oral administration in solid or liquid form or for rectal administration.

The pharmaceutical compositions of this invention can be administered to humans and other animals orally or rectally. Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) disintegrating agents such as agar-agar, calcium carbonate, potato or tapioca starch, alginic acid, certain silicates, and sodium carbonate, (d) solution retarding agents such as paraffin, (e) absorption accelerators such as quaternary ammonium compounds, and (f) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active agent can also be in micro-encapsulated form, if appropriate, with one or more of the above-mentioned excipients.

Compositions for rectal or vaginal administration are preferably suppositories which can be prepared by mixing the compounds of this invention with suitable non-irritating excipients or carders such as cocoa butter, polyethylene glycol, or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

A particularly preferred pharmaceutical compositions of the present invention comprise a dosage form of terazosin monohydrochloride in which the active drug component is dissolved or suspended in a liquid, non-aqueous pharmaceutical carrier encapsulated within a soft elastic capsule (SEC) shell. This preferred formulation comprises a unit dosage form comprising an outer soft elastic gelatin shell, and an inner composition filling said shell comprising a) an active drug component comprising the novel crystalline anhydrous polymorph of 1-(4-amino-6,7-dimethoxy-2-quinazolinyl)-4-(tetrahydro-2-furoyl)piperazine monohydrochloride of this invention characterized by the powder X-ray diffraction pattern, $^{13}C$ nuclear magnetic resonance spectrum, infrared spectrum, and differential scanning calorimetric thermogram of FIGS. 3, 6, 9, and 12 show, respectively and b) a pharmaceutically acceptable non-aqueous liquid carrier. A particularly preferred non-aqueous liquid carrier is poly(ethylene glycol).

The outer soft elastic shell comprises gelatin which is plasticised by the addition of glycerin, sorbitol or other polyol. The preferred capsule composition of the formulations of this invention comprises primarily a gelatin/glycerin mixture ranging between about 50 weight percent gelatin to about 60 weight percent gelatin, with about 55 to 58 weight percent gelatin being preferred. Small amounts of antimicrobial or antifungal agents such as methylparaben, propylparaben and mixtures of the alkylparabens are also present in amounts ranging between about 0.25 weight percent to about 0.4 weight percent, preferably about 0.3 weight percent of the total soft gelatin capsule shell weight. Flavoring agents are optionally added to the soft elastic gelatin capsule formula in amounts ranging between about 0.25 weight percent to about 0.4 weight percent, preferably about 0.3 weight percent of the total soft gelatin capsule shell weight to provide a pleasant taste to the capsule formulation. A preferred flavoring agent for formulations in accordance with the present invention is ethyl vanillin.

Opacifying or coloring agents such as titanium dioxide or iron oxide are also optionally added in amounts ranging between about 0.25 weight percent to about 0.5 weight percent, preferably about 0.3 weight percent of the total soft gelatin capsule shell weight to provide the desired color or opacity to the soft gelatin shell. When white titanium dioxide is used as the opacifying agent, various pharmaceutically acceptable dyes such as FD&C Blue, D&C Yellow, and FD&C Red may also be added to obtain the desired final color of the gelatin shell for identification purposes.

The inner fill composition of the formulations of the present invention comprises from between 1 and 15 mg of 1-(4-amino-6,7-dimethoxy-2-quinazolinyl)-4-(2-tetrahydrofuroyl)piperazine or a pharmaceutically acceptable salt thereof, with the hydrochloride salt being particularly preferred. The active drug component is dissolved and/or suspended in an inert, non-aqueous, pharmaceutically acceptable liquid carrier. Preferred carriers are selected from the polyethylene glycols, known in the trade as "PEG's," particularly PEG's having an average molecular weight in the range between about 200 and 600, with PEG 400 being most preferred. The liquid fill comprises from about 80–300 mg of PEG with the typical amount of PEG ranging between about 90–110 mg. The carrier may also include viscosity-building agents such as polyvinylpyrrolidone or silica gel and agents which enhance the suspendability of the drug component in the liquid carrier. Small amounts of glycerin, ranging between about 1–4 weight percent, preferably about 1.5–2 weight percent, based upon the total weight of the fill composition, may also be added to the liquid carder to retard the migration of glycerin out of the soft elastic gelatin capsule shell into the inner liquid fill.

The SEC formulations of the present invention are generally prepared by methods well known in the formulation arts. See, for example "Remington's Pharmaceutical Sciences," 18th Edition, A. Gennaro, Ed., Mack Publishing Co., Easton, Pa. 1990, pp.1662–1663. The capsules may be made by the so-called "plate process" in which a warm sheet of plasticized gelatin is placed on one of two molds containing depressions into which the drug fill is placed. A second sheet of warm gelatin and the second half of the mold is placed over the first and the sandwich pressed to form the soft elastic capsules. This technique permits the formation of soft elastic capsules in which the two halves of the capsule may be of different color for identification purposes.

In the so-called rotary-die process, two ribbons of gelatin are fed continuously into a rotating die assembly which converge adjacent to a fill-injector. The two gelatin ribbons are simultaneously formed into the two halves of the capsule which are filled and subsequently sealed as the die assembly rotates. The fill-injector is actuated by a pump which measures and dispenses the appropriate volume (dose) of the active drug component. This process permits accurate and reproducible formulations.

When formulated into the referred SEC pharmaceutical dosage form and administered to healthy human subjects, the new crystalline polymorph of terazosin monohydrochloride of this invention exhibits an observably diminished "food effect" when compared with dosage forms comprising the prior art dihydrate form. By the term "food effect" is meant differences between the times required to reach peak blood serum concentrations and the peak serum concentrations of the drug following administration to a fasting patient as opposed to administration postprandially.

The novel crystalline polymorph of terazosin monohydrochloride of the present invention was administered to 35 healthy human subjects in a soft elastic gelatin capsule dosage form. A significantly lower "food effect" was observed with the administration of this crystalline modification when compared with similar administration of the prior art tablet form of 1-(4-amino-6,7-dimethoxy-2-quinazolinyl)4-(tetrahydro-2-furoyl)-piperazine monohydrochloride dihydrate. In each case, 2 mg of terazosin was administered to subjects thirty minutes after eating and to the subjects in the fasting state. The serum levels of terazosin were measured, together with the maximum serum concentration ($C_{max}$) and the time required to reach maximum serum concentration ($t_{max}$). The data appear in Table 1.

TABLE 1

| Effect of Food on Bioavailability of Terazosin Administered in the Tablet v. Soft Gelatin Capsule Formulations | | | | |
|---|---|---|---|---|
| Parameter | SEC Formulation (Fasting) | SEC Formulation (Postprandial) | Prior Art Formulation (Fasting) | Prior Art Formulation (Postprandial) |
| $C_{max}$ (µM) | 40.70 ± 9.4 | 43.33 ± 8.8 | 41.85 ± 22.39 | 31.01 ± 11.27 |
| $t_{max}$ (Hrs.) | 1.2 | 1.9 | 1.3 | 2.4 |

The data in Table 1 show that there is only a small difference in the maximum serum concentration of 1-(4-amino-6,7-dimethoxy-2-quinazolinyl)-4-(tetrahydro-2-furoyl)-piperazine monohydrochloride administered to either a fasting patient or postprandially by means of the SEC formulation. Moreover, there is only a 0.7 hour difference in the time required to reach maximum serum concentration of terazosin administered by means of the SEC formulation of the present invention.

However, when terazosin monohydrochloride dihydrate is administered by means of the prior art tablet formulation, there is an observable difference in the maximum serum concentration when administered postprandially versus administration to a fasting patient. In this case, under the test conditions, there is also an approximate doubling of the time required for the postprandial dose of terazosin to reach maximum serum concentration. This "food effect" difference between the prior an tablet formulation for terazosin and the SEC formulation is surprising and appears not to be simply the result of the difference in the dosage forms.

The present invention also includes the use of the novel crystalline polymorph of terazosin monohydrochloride in the treatment of hypertension, congestive heart failure, and benign prostatic hyperplasia. In these uses, the compound is administered to subjects in need of such treatment in amounts ranging between about 0.5 mg to about 20 mg, preferably in the range of between about 1 mg and 10 mg per day, and most preferably in the range of about 1 mg to 5 mg per day. The actual dose administered in a particular case will depend upon the weight and physical condition of the patient and the severity of the disease condition. However, it is well within the skill of the physician to begin administration with a low dose and gradually increase the dose until the desired therapeutic effect is achieved.

The following examples are provided to enable one skilled in the art to practice the present invention, but should not be read as limiting the scope of the invention as it is defined by the appended claims.

EXAMPLE 1

Preparation of the Anhydrous Crystalline Polymorph of Terazosin Monohydrochloride of This Invention—Suspension Method Acetone was carefully dried for 48 hours at room temperature over molecular sieves (4 Å pore size) which had been previously dried at 190° C. The acetone was then decanted and further dried by contacting with anhydrous sodium sulfate for an additional 12 hours. Alternatively, the acetone may be decanted from the molecular sieves and filtered through a pad of anhydrous sodium sulfate.

Terazosin dihydrate monohydrochloride (1 g) was suspended in 10 ml of this previously dried acetone and the mixture thoroughly shaken and then allowed to stand for a period of 48 hours. At the end of this time the solid was collected by filtration and air dried. The material was analyzed by X-ray powder diffraction and shown to comprise approximately 45% of the new crystalline polymorph.

EXAMPLE 2

Preparation of the Anhydrous Crystalline Polymorph of Terazosin Monohydrochloride of this Invention—Solution Method Dry acetone and dry methanol were separately prepared by drying for 48 hours at room temperature by the method detailed in Example 1 above. Terazosin monohydrochloride dihydrate (3 gm, 6.5 mmol) was stirred in 100 mL of the dried methanol at ambient temperature until a clear solution was obtained. The previously dried acetone was carefully added to the resulting solution until a slight haze developed in the mixture. The mixture was allowed to stand until the terazosin hydrochloride precipitated. Solid anhydrous terazosin monohydrochloride (2.5 g, 5.9 mmol, 90% yield) was obtained. Thermogravimetric analysis indicated that the material did not contain any water or other solvent of crystallization. The powder X-ray diffraction pattern of the material indicated that it was free of detectable amounts of either the dihydrate starting material or the prior art anhydrate crystalline form.

EXAMPLE 3

Preparation of the Anhydrous Crystalline Polymorph of Terazosin Monohydrochloride of This Invention—Reflux Method To a 2-liter round-bottom flask containing 71.0 g (0.15 mol) of terazosin monohydrochloride dihydrate was added 1300 mL of absolute ethanol, a stirring bar and several glass boiling beads. The flask was fitted with a Dean-Stark trap and reflux condensor. The heterogenous mixture was heated under reflux for two days. After cooling, the undissolved white solid remaining in the flask was collected by vacuum filtration and washed with dry acetone to yield 60.9 g (0.143 mol, 93.5%) of the anhydrous crystalline polymorph of terazosin of this invention. The material was found by its powder x-ray diffraction pattern to be free of both the prior art anhydrous crystalline modification and the dihydrate form.

EXAMPLE 4

Preparation of the Anhydrous Crystalline Polymorph of Terazosin Monohydrochloride of This Invention—Reflux Method To a 500-mL round-bottom flask containing 5.19 g (0.011 mol) of terazosin monohydrochloride dihydrate was added 250 mL of dry acetone and several glass boiling beads. The flask was fitted with a Dean-Stark trap and reflux condensor. The heterogenous mixture was heated under reflux for five days. After cooling, the undissolved white solid remaining in the flask was collected by vacuum filtration to yield 4.3 g (0.010 mol, 90.9% yield) of the anhydrous crystalline polymorph of terazosin of this invention. The material was found by its powder x-ray diffraction pattern to be free of both the prior art anhydrous crystalline modification and the dihydrate form.

EXAMPLE 5

Preparation of the Anhydrous Crystalline Polymorph of Terazosin Monohydchoride of This Invention—Recrystallization of the Crystalline Dihydrate Terazosin monohydrochloride dihydrate (620 mg, 1.35 mmol) was dissolved in 100 mL of hot absolute ethanol in a 250 mL Erlenmeyer flask fitted with a ground glass joint. The solution was slowly cooled to room temperature and allowed to stand overnight. The resulting white crystalline precipitate was collected by vacuum filtration to yield 100 mg (0.24 mmol, 17.4%) of the anhydrous crystalline polymorph of terazosin of this invention. The material was found by its powder x-ray diffraction pattern to be free of both the prior art anhydrous crystalline modification and the dihydrate form.

EXAMPLE 6

Preparation of the Anhydrous Crystalline Polymorph of Terazosin Monohydrochloride of This Invention—Recrystallization of the Crystalline Anhydrate "Form I" from Ethanol Crystalline anhydrous form I terazosin monohydrochloride (1.0 g, 2.36 mmol) was dissolved in 175 mL of hot absolute ethanol in a 250 mL Erlenmeyer flask fitted with a ground glass joint. The solution was slowly cooled to room temperature and allowed to stand overnight. The resulting white crystalline precipitate was collected by vacuum filtration to yield 0.52 g (1.23 mmol, 51.9%) of the anhydrous crystalline polymorph of terazosin of this invention. The material was found by its powder x-ray diffraction pattern to be free of both the prior art anhydrous crystalline modification and the dihydrate form.

EXAMPLE 7

Preparation of the Anhydrous Crystalline Polymorph of Terazosin Monohydrochloride of This Invention—Recrystallization of the Crystalline Anhydrate "Form I" from Methanol Crystalline anhydrous form I terazosin monohydrochloride (500 mg (1.18 mmol) (obtained by the method disclosed in U.S. Pat. No. 4,026,894) was dissolved in a minimum amount of 175 mL of dry methanol. The solution was allowed to stand several weeks and the resulting white crystalline precipitate was collected by vacuum filtration to yield 300 mg (0.71 mmol, 60.2%) of the anhydrous crystalline polymorph of terazosin of this invention. The material was found by its powder x-ray diffraction pattern to be free of both the prior art anhydrous crystalline modification and the dihydrate form.

EXAMPLE 8

Preparation of the Anhydrous Crystalline Polymorph of Terazosin Monohydrochloride of This Invention—Recrystallization Of the Amorphous Form from Ethanol Amorphous terazosin monohydrochloride (747 mg, 1.76 mmol, obtained by drying the dihydrate monohydrochloride crystalline form at 110° C. for about three hours) was dissolved in the minimum amount of hot absolute ethanol. (The amorphous modification may also be obtained by lyophilization of an aqueous solution of terazosin monohydrochloride dihydrate.) The resulting solution was cooled to room temperature and allowed to stand overnight. The crystals which separated were collected by vacuum filtration and washed twice with 10 mL portions of dry acetone to yield 330 mg (0.77 mmol, 43.8% yield) of solid which was found by x-ray diffraction analysis to comprise 90% the anhydrous crystalline polymorph of terazosin of this invention.

We claim:

1. A process for the preparation of anhydrous crystalline 1-(4-amino-6,7-dimethoxy-2-quinazolinyl)-4-(tetrahydro-2-furoyl)piperazine monohydrochloride form II which comprises contacting a material selected from the group consisting of crystalline 1-(4-amino-6,7-dimethoxy-2-quinazolinyl)-4-(tetrahydro-2-furoyl)piperazine monohydrochloride dihydrate, crystalline 1-(4-amino-6,7-dimethoxy-2-quinazolinyl)-4-(tetrahydro-2-furoyl)piperazine monohydrochloride anhydrate form I, and amorphous 1-(4-amino-6,7-dimethoxy-2-quinazolinyl)-4-(tetrahydro-2-furoyl)piperazine monohydrochloride with an anhydrous polar organic solvent selected from the group consisting of alcohols of one to six carbon atoms, ketones of three to six carbon atoms, and mixtures thereof, followed by removal of the solvent to recover the solid product.

2. The process of claim 1 wherein the step of contacting said material with a polar organic solvent comprises heating crystalline 1-(4-amino-6,7-dimethoxy-2-quinazolinyl)-4-(tetrahydro-2-furoyl)piperazine monohydrochloride dihydrate under reflux in said solvent.

3. The process of claim 1 wherein the step of contacting said material with a polar organic solvent comprises dissolving said material in said solvent and precipitating the solid product from the resulting solution.

4. The process of claims 1-3 where said organic solvent is selected from the group consisting of $C_1$-$C_6$ alcohols, $C_3$-$C_6$ ketones and mixtures thereof.

5. The anhydrous crystalline polymorph of 1-(4-amino-6,7-dimethoxy-2-quinazolinyl)-4-(tetrahydro-2-furoyl)piperazine monohydrochloride which is the product of heating 1-(4-amino-6,7-dimethoxy-2-quinazolinyl)-4-(tetrahydro-2-furoyl)piperazine monohydrochloride dihydrate under reflux in a solvent selected from the group consisting of $C_1$-$C_6$ alcohols, $C_3$-$C_6$ ketones and mixtures thereof, followed by removal of the solvent.

6. The anhydrous crystalline polymorph of 1-(4-amino-6,7-dimethoxy-2-quinazolinyl)-4-(tetrahydro-2-furoyl)piperazine monohydrochloride which is the product of recrystallizing amorphous 1-(4-amino-6,7-dimethoxy-2-quinazolinyl)-4-(tetrahydro-2-furoyl)piperazine monohydrochloride dihydrate from a solvent selected from the group consisting of $C_1$-$C_6$ alcohols and $C_3$-$C_6$ ketones and mixtures thereof.

7. The anhydrous crystalline polymorph of 1-(4-amino-6,7-dimethoxy-2-quinazolinyl)-4-(tetrahydro-2-furoyl)piperazine monohydrochloride which is the product of recrystallizing 1-(4-amino-6,7-dimethoxy-2-quinazolinyl)-4-(tetrahydro-2-furoyl)piperazine monohydrochloride form I from a solvent selected from the group consisting of $C_1$-$C_6$ alcohols and $C_3$-$C_6$ ketones and mixtures thereof.

8. The anhydrous crystalline polymorph of 1-(4-amino-6,7-dimethoxy-2-quinazolinyl)-4-(tetrahydro-2-furoyl)piperazine monohydrochloride which is the product of recrystallizing amorphous 1-(4-amino-6,7-dimethoxy-2-quinazolinyl)-4-(tetrahydro-2-furoyl)piperazine monohydrochloride from a solvent selected from the group consisting of $C_1$-$C_6$ alcohols and $C_3$-$C_6$ ketones and mixtures thereof.

9. A pharmaceutical formulation useful for the treatment of hypertension, benign prostatic hyperplasia or congestive heart failure comprising a therapeutically effective amount of the product of claim 5 in combination with a pharmaceutically acceptable carrier.

10. A pharmaceutical formulation useful for the treatment of hypertension, benign prostatic hyperplasia or congestive heart failure comprising a therapeutically effective amount of the product of claim 6 in combination with a pharmaceutically acceptable carrier.

11. A pharmaceutical formulation useful for the treatment of hypertension, benign prostatic hyperplasia or congestive heart failure comprising a therapeutically effective amount of the product of claim 7 in combination with a pharmaceutically acceptable carrier.

12. A pharmaceutical formulation useful for the treatment of hypertension, benign prostatic hyperplasia or congestive heart failure comprising a therapeutically effective amount of the product of claim 8 in combination with a pharmaceutically acceptable carrier.

13. The anhydrous crystalline polymorph of 1-(4-amino-6,7-dimethoxy-2-quinazolinyl)-4-(tetrahydro-2-furoyl)piperazine monohydrochloride which is the product of contacting a material selected from the group consisting of crystalline 1-(4-amino-6,7-dimethoxy-2-quinazolinyl)-4-(tetrahydro-2-furoyl)piperazine monohydrochloride dihydrate, crystalline 1-(4-amino-6,7-dimethoxy-2-quinazolinyl)-4-(tetrahydro-2-furoyl)piperazine monohydrochloride anhydrate form I, and amorphous 1-(4-amino-6,7-dimethoxy-2-quinazolinyl)-4-(tetrahydro-2-furoyl)piperazine monohydrochloride with an anhydrous polar organic solvent selected from the group consisting of alcohols of one to six carbon atoms, ketones of three to six carbon atoms, and mixtures thereof, followed by removal of the solvent to recover the solid product.

* * * * *

UNITED STATES PATENT AND TRADEMARK OFFICE
CERTIFICATE OF CORRECTION

PATENT NO. : 5,362,730
DATED : November 8, 1994
INVENTOR(S) : JOHN F. BAUER; JAMES A. MORLEY It is certified that error appears in the above-indentified patent and that said Letters Patent is hereby corrected as shown below:

COLUMN 10, LINE 22: After the word "recrystallizing" delete the word --amorphous--.

Signed and Sealed this

Eleventh Day of April, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,362,730
DATED : November 8, 1994
INVENTOR(S) : J. F. Bauer, et al.

It is certified that error appears in the above-indentified patent and that said Letters Patent is hereby corrected as shown below:

Title page, replace:

"Notice: The portion of the term of this patent subsequent to Mar. 15, 2011 has been disclaimed."

with:

--Notice: The term of this patent shall not extend beyond the expiration date of Pat. No. 5,294,615.--

Signed and Sealed this

Third Day of June, 1997

*Attest:*

BRUCE LEHMAN

*Attesting Officer*     *Commissioner of Patents and Trademarks*